United States Patent [19]
Timmer et al.

[11] Patent Number: 5,837,321
[45] Date of Patent: Nov. 17, 1998

[54] VOLATILE ORGANIC LANTHANIDE COMPOUNDS AND METHODS FOR THE PREPARATION OF LANTHANIDE-CONTAINING LAYERED MATERIALS FORM THESE COMPOUNDS

[75] Inventors: Klaas Timmer, Bilthoven, Netherlands; Stephen L. Cook, Chester, Great Britain; Carolus Spee, Helmond, Netherlands

[73] Assignee: The Associated Octel Company Limited, London, England

[21] Appl. No.: 640,902

[22] PCT Filed: Nov. 24, 1994

[86] PCT No.: PCT/GB94/02576

§ 371 Date: Aug. 2, 1996

§ 102(e) Date: Aug. 2, 1996

[87] PCT Pub. No.: WO95/14698

PCT Pub. Date: Jun. 1, 1995

[30] Foreign Application Priority Data

Nov. 24, 1993 [NL] Netherlands .............. 9302030

[51] Int. Cl.$^6$ .................................................. C23C 16/18
[52] U.S. Cl. ................................ 427/248.1; 427/255.3; 427/226
[58] Field of Search ............... 427/248.1, 255.3, 427/226; 534/15

[56] References Cited

U.S. PATENT DOCUMENTS

| | | | |
|---|---|---|---|
| 5,028,724 | 7/1991 | Ivankovits et al. | 556/40 |
| 5,200,388 | 4/1993 | Abe et al. | 505/1 |
| 5,453,494 | 9/1995 | Kirlin et al. | 534/15 |
| 5,504,195 | 4/1996 | Leedham et al. | 534/15 |

FOREIGN PATENT DOCUMENTS

| | | |
|---|---|---|
| 0527661 | 2/1993 | European Pat. Off. . |
| 527661 | 2/1993 | European Pat. Off. . |
| 2274456 | 7/1994 | United Kingdom . |
| 8907666 | 8/1989 | WIPO . |

OTHER PUBLICATIONS

CA99:30325w, Gavrishchuk, et al., p. 486, 25 Jul. 1983.
CA119:194408h, Drake, et al., p. 993, 01 Nov. 1993.
CA113:90325p, Ponclet, et al., p. 817, 03 Sep. 1990.
CA105:202067z, Dzubenko, et al., p. 745, 01 Dec. 1986.
CA102: 16524j, Trembovetskii, p. 664, 14 Jan. 1985.
CA101:180535p, Gavrishchuk, et al., p. 686, 12 Nov. 1984.
CA93:214661k, Khan, et al., p. 695, 01 Dec. 1980.
CA109:182505t, Kuz'mina, et al., p. 837, 14 Nov. 1988.
CA119:261508f, Gleizes, et al., p. 881, 13 Dec. 1993.
CA119:151111p, Trikha, et al., p. 851, 04 Oct. 1993.
CA88:31390y, Murav'eva, et al., p. 556, 23 Jan. 1978.
CA116:74703s, Shiokawa, et al., p. 1047, 24 Feb. 1992.
CA119:240398e, Drake, et al., p. 1062, 29 Nov. 1993.
Iftikar, K, et al., "Mixed Ligand Complexes of Trivalent Lanthanide Ions with beta–Diketones and Heterocyclic Amines," Inorganic Chemistry, vol. 21, No. 1, 1982, pp. 80–84 (no month).
Mattson et al., Journal of the Less Common Metals, 112, pp. 373–380 (no month), 1985.
Cook et al., Journal de Physique IV, vol. 5, C5–407 to C5–414, Jun. 1995.

Primary Examiner—Michael Lusignan
Assistant Examiner—Timothy Meeks
Attorney, Agent, or Firm—Fay, Sharpe, Beall, Fagan, Minnich & McKee

[57] ABSTRACT

An adduct of a lanthanide (yttrium) β-diketonate and a donor ligand (N-oxide), the adduct being suitable for use in a metal-containing material deposition process, wherein the ligand has Lewis base characteristics that match the Lewis acid characteristics of the lanthanide β-diketonate in the absence of the ligand is described.

11 Claims, 2 Drawing Sheets

VOLATILE ORGANIC LANTHANIDE COMPOUNDS AND METHODS FOR THE PREPARATION OF LANTHANIDE-CONTAINING LAYERED MATERIALS FORM THESE COMPOUNDS

The present invention relates to volatile organic lanthanide compounds (adduct complexes) and methods for the preparation of lanthanide-containing layered materials from those compounds.

In particular, the present invention relates to volatile organic yttrium compounds. In this specification, the term lanthanide includes yttrium as well as all the elements (metals) with atomic numbers 57–71. Lanthanide elements 57–71 in particular are used in opto-electronic materials.

BACKGROUND OF THE INVENTION

Lanthanide compounds, especially lanthanide beta-diketonate complexes are of particular interest as starting materials (precursors) for so-called metal-organic chemical vapour deposition (MOCVD) of lanthanide (e.g. yttrium)-containing materials. Important examples are the deposition of mixed metal oxides which are superconducting at relatively high temperatures, of buffer layers, of anode- and electrolyte materials for fuel cells and of magnetic oxides.

Under some circumstances deposition of pure metal may he possible and the term metal-containing materials as used herein is to be interpreted accordingly. More than one metal may be present in the metal-containing material (normally metal oxide).

P. Lu, J. Zhao, C. S. Chern, Y. Q. Li, G. A. Kulesha, B. Gallois, P. Norris, B. Kear and F. Cosandey for instance, in J. Mater. Res., 7 (1992) 1993, describe the use of the 2,2,6,6-tetramethyl-3,5-heptanedione (TMHD) complex of Y, that is $Y(TMHD)_3$, as a precursor for yttrium during MOCVD of 90° K. superconducting $YBa_2Cu_3O_{7-x}$. However, in J. Phys., 50:C5 (1989) 981 (L. G. Hubert-Pfalzgraf, M. C. Massiani, R. Papiernik and O. Poncelet) and in Appl. Organomet. Chem., 6 (1992) 627 (L. G. Hubert-Pfalzgraf) there is described how water, always present in precursors, and also in this (commercially available) compound, can lead to hydrolysis during evaporation in a MOCVD process, with the consequence that the mass transport is not constant during the whole process. In addition, $Y(TMHD)_3$ has a rather high melting point (170° C.), which means that it is evaporated from the solid phase. Due to the appearance of differences in crystal shape and crystal size, varying evaporation rates can occur.

Also other volatile, though fluorine-containing, yttrium-β-diketonates are used, such as yttrium-6,6,7,7,8,8,8-heptafluoro-2,2-dimethyl-3.5-octanedionate monohydrate—$Y(FOD)_3 \cdot H_2O$—, for example in J. Mater. Res., 5 (1990) 2706 (D. J. Larkin, L. V. Interrante and A. Bose). This compound also contains water and, moreover, gives problems in the deposition of layers and their properties due to the presence of fluorine.

In J. Phys., 50:C5 (1989) 981 (L. G. Hubert-Pfalzgraf, M. C. Massiani, R. Papiernik and O. Poncelet), the easy formation of a coordination complex between an $Y(\beta$-diketonate$)_3$ and for instance dimethylformamide, pyridine or dimethylsulphoxide, is suggested, but no actual examples with $Y(TMHD)_3$ are given. The existence of a number of $Ln(TMHD)_3 \cdot DMF$ (Ln is a lanthanide metal) adducts is reported in Inorg. Synth., 11 (1968) 94 (K. J. Eisentraut and R. E. Sievers) and in Inorg. Chem., 6 (1967) 1933 (J. E. Schwarberg, D. R. Gere, R. E. Sievers and K. J. Eisentraut), but the compound $Y(TMHD)_3 \cdot DMF$ is not described.

WO 89/07666 (T. J. Marks and K. H. Dahmen) describes three Y precursors. The first is $Y(TMHD)_3$ but this is non ideal as it has a high melting point (175°–6° C.) and is mildly moisture sensitive. The second is $Y(FOD)_3$ (FOD= $C_3F_7COCHCOC(CH_3)_3$) but this has a high melting point and also contains fluorine. The third is $Y(ACAC)_3$ (ACAC= $H_3CCOCHCOCH_3$) and this has insufficient thermal stability to be an acceptable precursor; it is also high melting (138°–140° C.).

CA 99: 30325w describes adduct complexes $ML_3Q$ (where Q=o-phenanthroline, bipyridyl and $Ph_3P=O$) but these are so labile that they fully disintegrate in the process of mass spectra acquisition. These complexes are not stable materials that can be volatilised intact under MOCVD conditions.

CA 105: 202067z discloses $M(ACAC)_3 \cdot nH_2O$ and $M(ACAC)_3$.phen. Apparently, the phenanthroline adduct is more thermally stable than the water adduct and is claimed to be sublimed quantitatively under high vacuum. Under mass spectroscopy conditions the phenanthroline adduct decomposes and loses volatile $M(ACAC)_3$, i.e. is indistinguishable from $Y(ACAC)_3$, and it is therefore not an ideal MOCVD precursor.

CA 119:194408h (S. R. Drake et al Inorg Chem 1993, 32, 4464) discoses the dimer $[\{Y(TMHD)_3\}_2 \cdot triglyme]$. This complex is intrinsically less volatile and requires high vacuum in order to sublime intact.

N. Ahmad et al Inorg Chem 1982, 21, 80 say that many adduct complexes of $Ln(FOD)_3 \cdot nL$ can be formed. The authors comment on the tendency of the adducts to dissociate. These complexes would therefore be unsuitable for processes such as MOCVD.

CA 119: 240398e (S. R. Drake et al, J Chem Soc Dalton Trans 1993, 2379) suggests a tridentate donor could be bound to La (ionic radius 1.15—versus Y 0.93). However, this complex would be unsuitable for MOCVD processes and the like as it is involatile and decomposes on attempted sublimation at 175°–195° C. to yield $[La(TMHD)_3]$.

CA: 151111p discloses the existence of some tris FOD chelates with 1-methylpiperazine as a Lewis base donor ligand. The properties of the complexes are not discussed.

CA 109: 182505t shows that for adduct complexes $Y(ACAC)_3 \cdot L$ (where $L=(Me_2N)_3P=O$ or $Ph_3P=O$), heating $M(ACAC)_3 \cdot L$ is accompanied by the transition into the gas phase of $M(ACAC)_3 \cdot L$ and the decomposition products $M(ACAC)_3$ and L, i.e. these adduct complexes do not volatilise intact.

CA 101: 180535p describes the fragmentation of $Ln(ACAC)_3 \cdot L$ and $Ln(TMHD)_3 \cdot L$, which involves loss of neutral ligand, during mass spectroscopy. It is yet further evidence that adduct complexes with L=phenanthroline, bipyridyl and $Ph_3P=O$ do not have the desired properties for MOCVD processes.

CA 102: 16524j shows that $Ln(ACAC)_3 \cdot nL$ where L=acetylacetoneimine, dissociate on attempted sublimation, leaving parent $Ln(ACAC)_3$ for Ln=Dy-Lu, Y. Likewise, these adduct complexes are unsuitable for MOCVD processes.

The present invention therefore seeks to overcome the problems of dissociation and hydrolysis of lanthanide β-diketonates or their Lewis base adducts during MOCVD processes.

According to a first aspect of the present invention there is provided an adduct of a lanthanide β-diketonate and a donor ligand, the adduct being suitable for use in a metal-containing material deposition process (preferably a MOCVD process) wherein the donor ligand has Lewis base characteristics that match the Lewis acid characteristics of the lanthanide β-diketonate in the absence of the donor ligand (i.e. without the donor ligand). Alternatively this product may be defined as a lanthanide β-diketonate complex with a complexing ligand.

According to a second aspect of the present invention there. is provided a metal-containing material deposition process/method (preferably a MOCVD process) comprising the use of an adduct of a lanthanide β-diketonate and a donor ligand wherein the donor ligand has Lewis base characteristics that match the Lewis acid characteristics of the lanthanide β-diketonate in the absence of the donor ligand.

According to a third aspect of the present invention there is provided the use of an adduct of a lanthanide β-diketonate and a donor ligand in a metal-containing material deposition process (preferably a MOCVD process) wherein the donor ligand has Lewis base characteristics that match the Lewis acid characteristics of the lanthanide β-diketonate in the absence of the donor ligand.

One or more ligands may be present.

Preferably the lanthanide (β-diketonate)-ligand adduct has a melting point of less than about 150° C., more preferably of less than about 125° C., even more preferably of less than about 100° C.

Preferably the adduct forming ligand is a neutral donor ligand.

Preferably the ligand is an oxide.

Preferably the oxide is an N-oxide.

Preferably the N-oxide is a pyridine N-oxide.

Preferably the lanthanide is yttrium.

Preferably the metal-containing material deposition process is a MOCVD process.

The donor ligand in the lanthanide β-diketonate adducts of the present invention has Lewis base characteristics that match the Lewis acid characteristics of the lanthanide β-diketonate in the absence of the ligand—as according to Pearson hard-soft acid-base theory (J. Am. Chem. Soc. 1963, 85, 3533).

Therefore, if the lanthanide β-diketonate without the donor ligand has a high charge density so does the donor ligand. Likewise, if the lanthanide β-diketonate without ligand has a low charge density so does the donor ligand.

SUMMARY OF THE INVENTION

The present invention is therefore based on the surprising finding that if the Lewis base characteristics of an adduct forming ligand match the Lewis acid characteristics of the lanthanide β-diketonate without the ligand then the resultant lanthanide (β-diketonate)—ligand adducts are particularly suited for use in metal deposition processes, in particular MOCVD processes.

DETAILED DESCRIPTION

Figure 1:
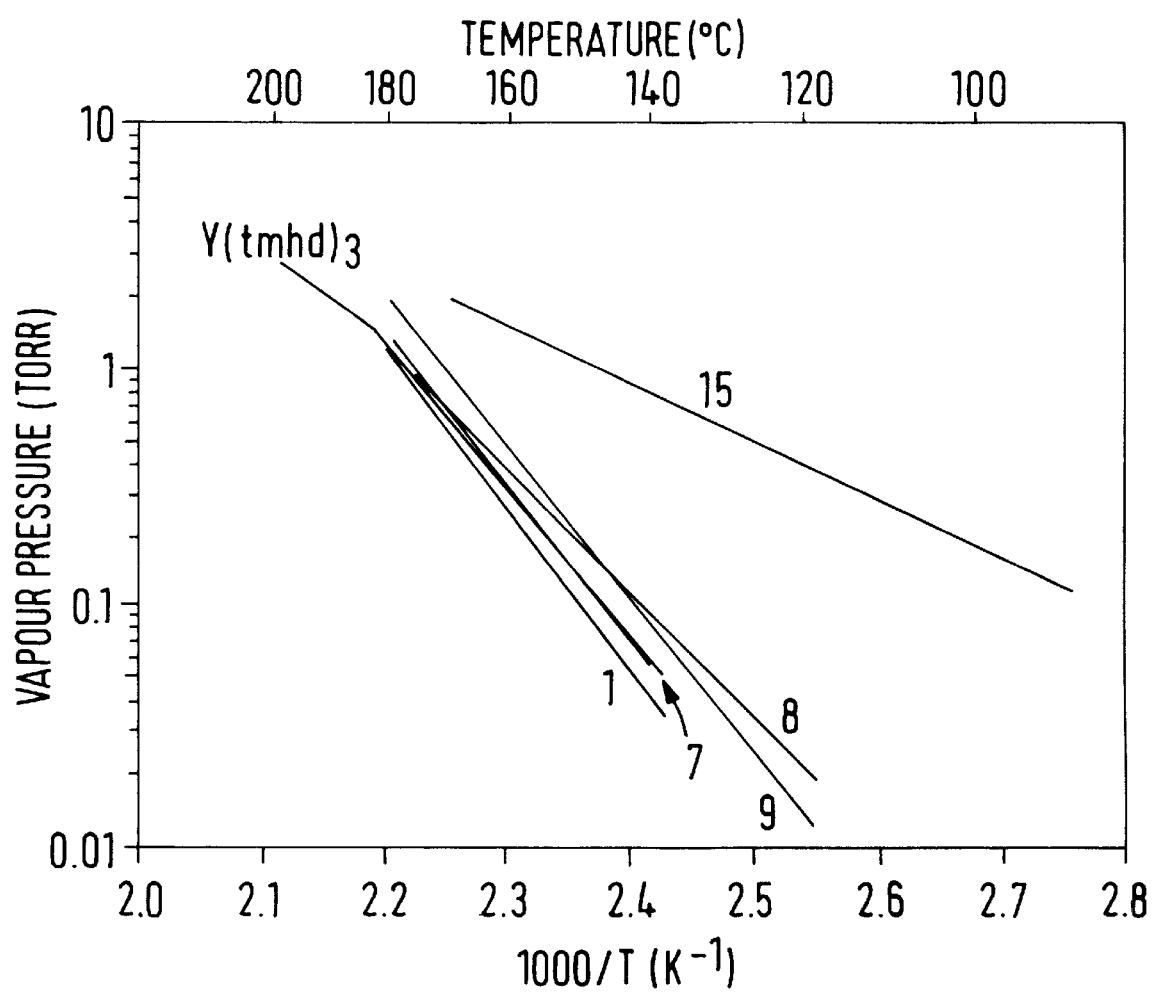
FIG. 1 represents a plot of vapor pressure as a function of temperature for compounds of the invention and a comparative compound.

A key advantage of some of the lanthanide (β-diketonate)—ligand adduct complexes of the present invention is that they have a low melting point (e.g. less than about 150° C., preferably less than about 125° C., more preferably less than about 100° C.). This means that those adduct complexes are liquid in use. This is particularly advantageous as the exposed surface area of the lanthanide adduct complex during the MOCVD process remains substantially constant. This is in direct contrast to the typically used metal complexes which are of a non-uniform particulate nature. With those particulate complexes, the smallest particles will evaporate initially leaving behind the larger particles. Hence, in the known process, the surface area of the exposed metal complex decreases and thus the evaporation rate decreases. Furthermore, sintering often occurs with the particles of the present invention during the MOCVD process with the result that the surface area:volume ratio, and therefore the evaporation rate, decreases even further. The lanthanide (β-diketonate)—ligand adduct complexes of the present invention permit these problems associated with the known MOCVD processes to be overcome or mitigated.

In addition, preferably the neutral (uncharged) donor ligand is an amine, a diamine, a polyamine, a pyridine, a dipyridine, a phenanthroline, an amide, a sulphoxide, an amine-N-oxide, a pyridine-N-oxide, a dipyridine-N,N-oxide, a phosphineoxide, an acyclic ether, a cyclic ether, a glycol ether, or a polyether, pyridine N-oxides and 4-alkyl pyridine N-oxides being especially preferred.

Of the other possibilities preferably the diamine is $(CH_3)_2NCH_2CH_2N(CH_3)_2$, the polyamine is $(CH_3)_2NCH_2CH_2N(CH_3)CH_2CH_2N(CH_3)_2$ or $(CH_3)_2NCH_2CH_2N(CH_3)CH_2CH_2N(CH_3)CH_2CH_2NCH_3)_2$, the pyridine is $C_5H_5N$, the dipyridine is o-$(2-C_5H_4N)C_5H_4N$, the phenanthroline is 1,10-phenanthroline (4,5-diazaphenanthrene), the amide is $(CH_3)_2NC(O)H$, the sulphoxide is $CH_3S(O)CH_3$, the amine-N-oxide is $(CH_3)_3NO$, and the phosphineoxide is $(C_5H_5)_3PO$ or $(C_2H_5)_3PO$.

Preferably the pyridine-N-oxide contains a substituted or unsubstituted alkyl group.

Preferably the substituent alkyl group is $C(CH_3)_3$ or $C_2H_5$.

Preferably the β-diketonate contains a substituted or unsubstituted alkyl group and/or a substituted or unsubstituted aryl group.

Preferably the alkyl group is $C(CH_3)_3$ or n-$C_3F_7$.

Preferably the deposition technique is the so-called metal organic chemical vapour deposition (MOCVD).

The organic lanthanide (e.g. yttrium) adducts may be formed by adding Lewis base ligand, in liquid or vapour phase, to the lanthanide (e.g. yttrium) -β-diketonate.

The organic lanthanide (e.g. yttrium) adducts may be transported into the reactor via a liquid-evaporation system.

Thus, the advantages of the adducts of the present invention, especially the yttrium adducts, are that they allow the afore-mentioned problems with the known volatile compounds to be overcome.

In this regard, the present invention is based on the surprising finding that the problems may be overcome by the combination of certain lanthanide (e.g. yttrium) -β-diketonates and coordinating neutral donor ligands according to the present invention.

Without excluding other deposition techniques such as metal-organic spray-pyrolysis (as an example), the method of the invention is particularly appropriate when applied with MOCVD.

By using volatile and stable compounds according to the invention as starting material ("precursor"), the MOCVD technique can be used in a simple manner for instance to prepare yttrium-containing materials. The applicability of MOCVD for-such materials is of importance especially for preparation of and research on, recently discovered, superconducting mixed metal oxides, buffer layers, anode and electrolyte materials for fuel cells and magnetic oxide materials.

In an alternative embodiment of the process/method according to the present invention the organic lanthanide (e.g. yttrium) adducts are formed during the MOCVD process by adding coordinating ligand in liquid or vapour phase to the lanthanide (e.g. yttrium) -β-diketonate (co-evaporation process). Also with this method an increased and more constant mass transport of the lanthanide (e.g yttrium) -β-diketonate can be obtained.

The present invention therefore provides new volatile organic lanthanide (e.g. yttrium) compounds, characterised in that they consist of the complex of a lanthanide (e.g. yttrium) -β-diketonate and one or more coordinating neutral donor ligands according to the present invention.

Suitable neutral donor ligands for the compounds of the present invention are:

amines, $RR^1R^2N$, with R, $R^1$, $R^2$=H and/or $C_1$–$C_4$ group(s);

di- and polyamines, $RR^1N(CH_2CH_2NR^2)_n$ $CH_2CH_2NR^3R^4$, with R, $R^1$, $R^2$, $R^3$, $R^4$=(substituted) alkyl, n=0–5, for instance tetramethylethylenediamine, pentamethyldiethylenetriamine, hexamethyltriethylenetetraamine and the like;

pyridines, $C_5R_nH_{5-n}N$, with R=$C_1$–$C_4$ group, n=0–5, for instance pyridine and the like;

dipyridines, for instance 2,2'-dipyridine and the like;

phenanthrolines, for instance 1,10-phenanthroline (4,5-diazaphenanthrene) and the like;

amides, $RR^1NC(O)H$, with R, $R^1$=(substituted)alkyl, for instance dimethylformamide (DMF) and the like;

sulphoxides, $RS(O)R^1$, with R and $R^1$ representing a $C_1$–$C_4$ group, for instance dimethylsulphoxide (DMSO) and the like;

amine-N-oxides, $RR^1R^2NO$, with R, $R^1$, $R^2$=H and/or $C_1$–$C_4$ group(s), for instance trimethylamine-N-oxide and the like;

pyridine-N-oxides, $C_5R_nH_{5-n}NO$, with R=$C_1$–$C_4$ group, n=0–5, for instance 4-ethylpyridine-N-oxide, 4-tert-butylpyridine-N-oxide and the like;

dipyridine-N,N-dioxides, $2,2'-(C_5R_nH_{4-n}NO)_2$, with R=$C_1$–$C_4$ group, n=0–4;

phosphineoxides, $RR^1R^2PO$, with R, $R^1$, $R^2$=H and/or $C_1$–$C_4$ group(s) and/or (substituted)aryl group(s), for instance triethyiphosphineoxide, triphenyliphosphineoxide and the like;

acyclic ethers, $ROR^1$, with R and $R^1$ representing a $C_1$–$C_4$ group, for instance diethylether, dibutylether and the like;

cyclic ethers, $(CRR^1)_nO$ and $[(CRR^1)_nO]_m$, with R, $R^1$=H and/or $C_1$–$C_4$ group(s), n, m=1–6, for instance tetrahydrofuran, dioxane, crown ethers such as 18-crown-6 and the like;

glycol ethers, $R^1-(OCHRCH_2)_nOR^2$, with R=H, Me, and $R^1$, $R^2$=(substituted)alkyl, n=1–6, for instance R=H, $R^1$=$R^2$=Me, glyme (n=1, dimethoxyethane, DME), diglyme (n=2), triglyme (n=3), tetraglyme (n=4), hexaglyme (n=6) and the like;

polyethers, $RO[(CR^1R^2)_nO]_mH$ and $RO[(CR^1R^2)_nO]_mR^3$, with R, $R^3$=(substituted)alkyl and $R^1$, $R^2$=H, (substituted)alkyl, n=1–4, m=1–6.

The adducts of the present invention, in particular those of the yttrium-β-diketonates according to the invention, possess a much higher stability to hydrolysis than the corresponding lanthanide (e.g. yttrium) -β-diketonates lacking the complexing neutral donor ligand, because due to the coordination of the neutral donor ligand, there is no coordination site left for water: the yttrium is coordinately saturated. As a consequence, hydrolysis during handling and the subsequent evaporation in a MOCVD process is prevented.

The synthesis of the lanthanide (e.g. yttrium) -β-diketonate-ligand adducts according to the invention proceeds via a reaction between the required quantity of ligand and the appropriate lanthanide (e.g. yttrium) -β-diketonate in an inert solvent, such as dichloromethane, or for example via crystallisation of the appropriate lanthanide (e.g. yttrium) -β-diketonate from the complexing ligand.

The stability of the adducts according to the invention is highest when the neutral donor ligand is a pyridine-N-oxide, an amine-N-oxide or a phosphineoxide; preferably the neutral donor ligand is a pyridine-N-oxide or an alkyl pyridine-N-oxide.

It has been found that the melting points of the adducts according to the invention are lowered when the neutral donor ligand contains at least one (substituted)alkyl group.

Preferably the lanthanide is tri-valent, such as yttrium. The following structural formulae therefore give a number of representative examples of lanthanide adducts according to the present invention:

$Ln\{(CH_3)_3CC(O)CHC(O)C(CH_3)_3\}_3 \cdot \{o\text{-}(2\text{-}C_5H_4N)C_5H_4N\}$. $Ln\{(CH_3)_3CC(O)CHC(O)C(CH_3)_3\}_3 \cdot \{1,10\text{-phenanthroline}\}$. $Ln\{(CH_3)_3CC(O)CHC(O)C(CH_3)_3\}_3 \cdot \{(CH_3)_2NCH_2CH_2N(CH_3)_2\}$. $Ln\{(CH_3)_3CC(O)CHC(O)C(CH_3)_3\}_3 \cdot \{(CH_3)_2NCH_2CH_2N(CH_3)CH_2CH_2N(CH_3)_2\}$. $Ln\{(CH_3)_3CC(O)CHC(O)C(CH_3)_3\}_3 \cdot \{(CH_3)_2N[CH_2CH_2N(CH_3)]_2CH_2CH_2N(CH_3)_2\}$. $Ln\{(CH_3)_3CC(O)CHC(O)C(CH_3)_3\}_3 \cdot \{(CH_3S(O)CH_3\}$. $Ln\{(CH_3)_3CC(O)CHC(O)C(CH_3)_3\}_3 \cdot \{C_5H_5NO\}$. $Ln\{(CH_3)_3CC(O)CHC(O)C(CH_3)_3\}_3 \cdot \{4\text{-}(tert\text{-}C_4H_9)C_5H_4NO\}$. $Ln\{(CH_3)_3CC(O)CHC(O)C(CH_3)_3\}_3 \cdot \{4\text{-}(C_2H_5)C_5H_4NO\}$. $Ln\{(CH_3)_3CC(O)CHC(O)C(CH_3)_3\}_3 \cdot \{(CH_3)_3NO\}$. $Ln\{(CH_3)_3CC(O)CHC(O)C(CH_3)_3\}_3 \cdot \{(C_6H_5)_3PO\}$. $Ln\{(CH_3)_3CC(O)CHC(O)C(CH_3)_3\}_3 \cdot \{(C_2H_5)_3PO\}$. $Ln\{(CH_3)_3CC(O)CHC(O)C(CH_3)_3\}_3 \cdot \{C_5H_5N\}$. $Ln\{(CH_3)_3CC(O)CHC(O)C(CH_3)_3\}_3 \cdot \{(CH_3)_2NC(O)H\}$. $Ln\{CF_3CF_2CF_2C(O)CHC(O)C(CH_3)_3\}_3 \cdot \{(CH_3)_2NCH_2CH_2N(CH_3)CH_2CH_2N(CH_3)_2\}$.

Figure 2:
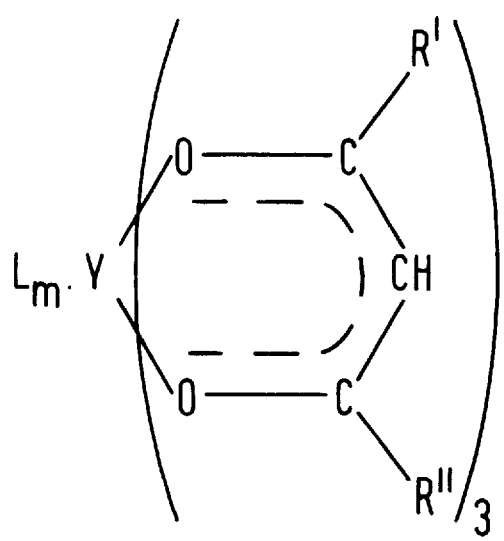
FIG. 2 represents the general structure of the lanthanide adducts of the invention.

The general structure formula of the preferred compounds according to the invention is given on the formula sheet (FIG. 2).

In this structural formula R' and R" represent the side chains of the diketonate, L represents the coordinating neutral donor ligand, and m the number of coordinating neutral donor ligands. R' and R" may be the same or different and each is preferably relatively bulky, for example $CF_3$, $C_3F_7$ or more preferably tert-$C_4H_9$.

As mentioned above, the Y(-β-diketonate)$_3$ compound Y(TMHD)$_3$, without neutral donor ligand, has a relatively high melting point. With some examples of adducts according to the invention, which have a much lower melting point than Y(TMHD)$_3$ itself, conditions can be realised under which, for instance in a MOCVD process, during a longer period of time (several days), a constant mass transport of yttrium compound per unit of time can be maintained.

In a preferred embodiment of the invention, the Y(β-diketonate) compound is Y(TMHD)$_3$ and the neutral donor ligand is pyridine-N-oxide, which contains at least one of the alkyl groups $C_2H_5$ or tert-$C_4H_9$.

With compounds according to this preferred embodiment, the most stable, volatile yttrium-β-diketonate-ligand adducts at elevated temperatures and/or lowered pressures are formed. They also are stable to hydrolysis in air and have low melting points.

The following structural formulae give a number of representative examples of yttrium compounds according to the present invention:

1. Y{(CH$_3$)$_3$CC(O)CHC(O)C(CH$_3$)$_3$}$_3$·{(o-(2-C$_5$H$_4$N}.
2. Y{(CH$_3$)$_3$CC(O)CHC(O)C(CH$_3$)$_3$}$_3$·{1,10-phenanthroline}.
3. Y{(CH$_3$)$_3$CC(O)CHC(O)C(CH$_3$)$_3$}$_3$·{(CH$_3$)$_2$NCH$_2$CH$_2$N(CH)$_3$)$_2$}.
4. Y{(CH$_3$)$_3$CC(O)CHC(O)C(CH$_3$)$_3$}$_3$·{(CH$_3$)$_2$NCH$_2$CH$_2$N(CH$_3$)CH$_2$CH$_2$N(CH$_3$)$_2$}.
5. Y{(CH$_3$)$_3$CC(O)CHC(O)C(CH$_3$)$_3$}$_3$·{(CH$_3$)$_2$N[CH$_2$CH$_2$N(CH$_3$)]$_2$CH$_2$CH$_2$N(CH$_3$)$_2$}.
6. Y{(CH$_3$)$_3$CC(O)CHC(O)C(CH$_3$)$_3$}$_3$·{CH$_3$S(O)CH$_3$}.
7. Y{(CH$_3$)$_3$CC(O)CHC(O)C(CH$_3$)$_3$}$_3$·{C$_5$H$_5$NO}.
8. Y{(CH$_3$)$_3$CC(O)CHC(O)C(CH$_3$)$_3$}$_3$·{4-(tert-C$_4$H$_9$)C$_5$H$_4$NO}.
9. Y{(CH$_3$)$_3$CC(O)CHC(O)C(CH$_3$)$_3$}$_3$·{4-(C$_2$H$_5$)C$_5$H$_4$NO}.
10. Y{(CH$_3$)$_3$CC(O)CHC(O)C(CH$_3$)$_3$}$_3$·{(CH$_3$)$_3$NO}.
11. Y{(CH$_3$)$_3$CC(O)CHC(O)C(CH$_3$)$_3$}$_3$·{(C$_5$H$_5$)$_3$PO}.
12. Y{(CH$_3$)$_3$CC(O)CHC(O)C(CH$_3$)$_3$}$_3$·{(C$_2$H$_5$)$_3$PO}.
13. Y{(CH$_3$)$_3$CC(O)CHC(O)C(CH$_3$)$_3$}$_3$·{(C$_5$H$_5$N}.
14. Y{(CH$_3$)$_3$CC(O)CHC(O)C(CH$_3$)$_3$}$_3$·{(CH$_3$)$_2$NC(O)H}.
15. Y{(CH$_3$)$_3$CC(O)CHC(O)C(CH$_3$)$_3$}$_3$·{(CH$_3$)$_2$NCH$_2$CH$_2$N(CH$_3$)CH$_2$CH$_2$N(CH$_3$)$_2$}.

The thermal stability of the compounds 1, 2, 7, 10–12 and 15 according to the invention (determined by Simultaneous Thermal Analysis [STA]) is shown in Table 1 (discussed later). As the table shows, these compounds evaporate intact at atmospheric pressure and at temperatures between 102° C. and 353° C. The highest amount of residue remaining afterwards is 2.06% (complex 9), clearly less than with commercially obtained Y(TMHD)$_3$ (4.40%). The melting peaks, found in the STA spectra, agree well with the actual melting points, as well as the observed volatilities.

The volatility and the melting points of the compounds 1-15, as well as those of the corresponding non-complexed yttrium-β-diketonates, are shown in Table 2 (discussed later). As the table shows, these compounds sublime at lowered pressure (0.01 to 0.05 mm Hg) and at temperatures between 90° C. and 200° C. The compounds 1, 2, 7–12 and 15 are thermally stable under these conditions and evaporate without dissociation. This means that they are especially suitable as a starting material (precursor) for the above mentioned "metal-organic chemical vapour deposition" (MOCVD) of yttrium containing materials. The compounds 3–6, 13 and 14 dissociate into Y(TMHD)$_3$ and free neutral donor ligand. This means that these compounds are suitable as MOCVD precursors in a so-called co-evaporation process, whereby extra neutral donor ligand is added to the carrier gas.

The low melting complexes 4 and 5 are also suitable in a process in which use is made of liquid-evaporation systems.

The vapour pressures as a function of the temperature of the compounds 1, 7–9 and 15, as well as those of Y(TMHD)$_3$, are plotted in FIG. 1 and shown in Table 3. As FIG. 1 and Table 3 show, the order of volatility is compound 15>>8, 9>Y(TMHD)$_3$, 7>1. This means that the yttrium compounds according to the invention, despite their much higher molecular mass as compared with Y(TMHD)$_3$, have a volatility which lies in the same order of magnitude and, in the case of compounds 8–9, the volatility is even somewhat higher. Compound 15 has a volatility which is many times higher than that of the compounds 1 and 7–9.

The compounds 8 and 9 according to the invention are of special interest. These adducts of the non-fluorine-containing complex Y(TMHD)$_3$ have a markedly lower melting point than Y(TMHD)$_3$ itself. As a consequence, in the MOCVD process, they may be evaporated from the liquid phase. In addition, they are somewhat more volatile than Y(TMHD)$_3$. This offers important advantages, especially concerning the realisation of a constant mass transport of the Y-compound in the MOCVD process.

The invention also provides a method for the preparation of layered materials which contain yttrium oxide, by means of a deposition technique.

Such a method is known, for example, from the publications of Lu and Hubert-Pfalzgraf et al., mentioned above.

With the known methods, in particular MOCVD, problems are sometimes encountered with the deposition of yttrium-containing layered structures, as a result of the presence of water in, and the resulting hydrolysis of, the starting material (the precursor) from which the deposition should take place.

The invention can be used to eliminate or mitigate these problems and provides a method, characterised in that in a deposition technique one starts with volatile yttrium adducts according to the invention described above.

Highly preferred embodiments of the present invention therefore include the following subject-matter or may be defined as follows.

1. Volatile organic yttrium compounds, characterised in that they consist of an adduct of an yttrium-β-diketonate and one or more coordinating neutral donor ligands.
2. A method for the preparation of layered materials which contain yttrium oxide, by means of a deposition technique, characterised in that in the deposition technique one starts with the volatile organic yttrium compounds according to the present invention.

The following examples illustrate the methods and chemical preparation of typical compounds according to the present invention. All reactions are carried out in a dry atmosphere and at room temperature unless stated otherwise.

EXAMPLE 1

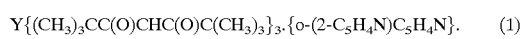

0.64 g (1.0 mmol) of Y(TMHD)$_3$ and 0.16 g (1.0 mmol) of bipy (2,2'-dipyridine) are dissolved in 15 ml of CH$_2$Cl$_2$. The resulting solution is stirred for 0.5,h and then evaporated to dryness. The residue is sublimed at 160°–170° C./0.06 mm Hg.

Yield: 0.63 g of colourless 1 (80.0%).
Melting point: 185°–188° C.
$^1$H NMR in CDCl$_3$: δ(Bu$^t$) 1.03 (s); δ(CH) 5.45 (s); δ(C$_5$H$_4$) 7.73, 7.79, 7.91 and 9.42 (m).

Elemental analysis: found (calculated) (%) C 65.02 (65.00); H 8.31 (8.19); N 3.63 (3.53).

STA: melting peak at 188° C.; evaporation from 155°–293° C.; a residue of 0.55% remains afterwards.

EXAMPLE 2

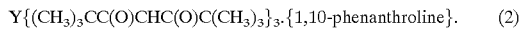

Prepared as described for 1 from 0.64 g (1.0 mmol) of Y(TMHD)$_3$ and 0.20 g (1.0 mmol) of phen.H$_2$O (1,10-phenanthroline monohydrate). The residue, obtained after evaporation of the solvent, is now sublimed at 180° C.–200° C./0.03 mm Hg.

Yield: 0.61 g of off-white 2 (75.3%).

Melting point: softening at 235° C. melting at 260°–262° C.

$^1$H NMR in CDCl$_3$: δ(Bu$^t$) 0.95 (s); δ(CH) 5.42 (s); δ(phen) 7.65 (m), 7.75 (s), 8.23 and 9.72 (m).

Elemental analysis: found (calculated) (%) C 65.71 (66.02); H 7.96 (7.95); N 3.55 (3.42).

STA: phase transition peak at 233° C.; melting peak at 269° C.; evaporation from 166°–353° C.; a residue of 1.22% remains afterwards.

EXAMPLE 3

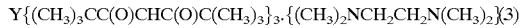

Prepared as described for 1 from 0.64 g (1.0 mmol) of Y(TMHD)$_3$ and 0.12 g (1.0 mmol) of Me$_2$NCH$_2$CH$_2$NMe$_2$. The residue, obtained after evaporation of the solvent, is not sublimed but dried in vacuo for 2 h.

Yield: 0.67 g of colourless 3 (89.3%).

Melting point: softening at 110°, melting at 145°–150° C.

$^1$H NMR in CDCl$_3$: δ(Bu$^t$) 1.08 (s); δ(CH) 5.67 (s); δ(NMe$_2$) 2.29 (s); δ(CH$_2$N) 2.53 (s).

Elemental analysis: found (calculated) (%) C 61.22 (62.08); H 9.11 (9.68); N 3.55 (3.71).

Sublimation: the complex does not sublime as such; at 150° C./0.03 mm Hg rapid dissociation occurs with evaporation of the diamine; the sublimate consists of Y(TMHD)$_3$ and a trace of the diamine ($^1$H NMR).

EXAMPLE 4

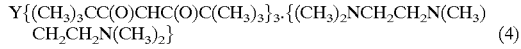

Prepared as described for 1 from 0.64 g (1.0 nmol) of Y(TMHD)$_3$ and 0.17 g (1.0 mmol) of the triamine. The residue, obtained after evaporation of the solvent, is not sublimed but dried in vacuo for 8 h.

Yield: 0.73 g of colourless 4 (90.1%).

Melting point: softening at 55° C., melting at 60°–63° C.

$^1$H NMR in CDCl$_3$: δ(Bu$^t$) 1.10 (s); δ(CH) 5.71 (s); δ(NMe$_2$) 2.29 (s); δ(NMe) 2.24 (s); δ(CH$_2$N) 2.49 and 2.54 (m).

Elemental analysis: found (calculated) (%) C 60.95 (62.15); H 9.84 (9.87); N 5.06 (5.18).

Sublimation: the complex does not sublime as such; at 90°–160° C./0.04 mm Hg dissociation occurs with evaporation of the ligand; the sublimate consists of Y(TMHD)$_3$ and 0.4 eq of the triamine ($^1$H NMR).

STA: melting peak at 62° C.; evaporation from 61°–290° C. (different evaporation rates observed); a residue of 1.3% remains afterwards.

EXAMPLE 5

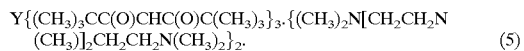

Prepared as described for 1 from 0.64 g (1.0 mmol) of Y(TMHD)$_3$ and 0.23 g (1.0 mmol) of the tetraamine. The residue, obtained after evaporation of the solvent, is not. sublimed but dried in vacuo for 1 h.

Yield: 0.86 g of off-white 5 (100%); partly solid.

Melting point: 55°–60° C.

$^1$H NMR in CDCl$_3$: δ(Bu$^t$) 1.10 (s); δ(CH) 57.2 (s) δ(NMe$_2$) 2.29 (s); δ(NMe) 2.26 (s); δ(CH$_2$N) 2.46 and 2.54 (m).

Elemental analysis: found (calculated) (%) C 60.57 (62.22); H 10.81 (10.02); N 10.18 (6.45); inhomogeneous.

Sublimation: the complex does not sublime as such; at 90°–130° C./0.04 mm Hg dissociation occurs with evaporation and condensation of the tetraamine; the sublimate consists of Y(TMHD)$_3$ and 2.4 eq of the tetraamine ($^1$H NMR).

EXAMPLE 6

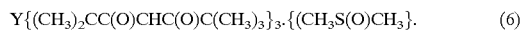

Prepared as described for 1 from 0.64 g (1.0 mmol) of Y(TMHD)$_3$ and 0.16 g (2.0 mmol) of DMSO. The residue, obtained after evaporation of the solvent, is not sublimed but dried in vacuo for 8 h.

Yield: 0.66 g of colourles6 (93.0%).

Melting point: 156°–158° C.

$^1$H NMR in CDCl$_3$: δ(Bu$^t$) 1.04 (s); δ(CH) 5.63 (s); δ(CH$_3$) 2.64.

Elemental analysis: found (calculated) (%) C 57.74 (58.66); H 8.71 (8.80); N 4.41 (4.48).

Sublimation: the complex does not sublime as such; at 135°–160° C./0.04 mm Hg dissociation occurs with evaporation of DMSO; the sublimate consists of Y(TMHD)$_3$ and 0.3 eq of DMSO ($^1$H NMR).

EXAMPLE 7

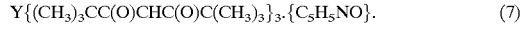

Prepared as described for 1 from 0.64 g (1.0 mmol) of Y(TMHD)$_3$ and 0.19 g (2.0 mmol) of pyNO (pyridine-N-oxide). The residue, obtained after evaporation of the solvent, is stirred with 100 ml of pentane for 15 minutes. The turbid solution is filtered and evaporated to dryness. The residue is sublimed at 150°–160° C./0.04 mm Hg.

Yield: 0.56 g of off-white 7 (76.7%).

Melting point: 175°–177° C.

$^1$H NMR in CDCl$_3$: δ(Bu$^t$) 1.05 (s); δ(CH) 5.62 (s); δ(pyNO) 7.32 (t), 7.45 (t), 8.55 (d).

Elemental analysis: found (calculated) (%) C 62.02 (62.22); H 8.30 (8.46); N 1.89 (1.91).

STA: melting peak at 179° C.; evaporation from 146°–288° C. a residue of 0.71% remains afterwards.

EXAMPLE 8

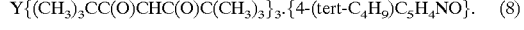

Prepared as described for 7 from 0.64 g (1.0 mmol) of Y(YMHD)$_3$ and 0.17 g (1.1 mol) of 4-Bu$^t$-pyNO (4-tertbutylpyridine-N-oxide). The residue, obtained after evaporation of the pentane solution, is now sublimed at ±140° C./0.03 mm Hg.

Yield: 0.6 g of colourless 8 (76.1%).
Melting point: 97°–100° C.
$^1$H NMR in $C_6D_6$: δ($Bu^n$TMHD) 1.27 (s); δ(CH) 5.94 (s); δ($Bu^t$-pyNO) 0.76 (s); δ(pyNO) 6.46 and 8.17 (d).
Elemental analysis: found (calculated) (%) C 64.47 (63.89); H 8.50 (8.87); N 1.99 (1.78).

EXAMPLE 9

Y{(CH$_3$)$_3$CC(O)CHC(O)C(CH$_3$)$_3$}$_3$.{4-(C$_2$H$_5$)C$_5$H$_4$NO}. (9)

Prepared as described for 7 from 0.64 g (1.0 mmol) of Y(TMHD)$_3$ and 0.13 g (1.05 mmol) of 4-Et-pyNO (4-ethylpyridine-N-oxide). The residue, obtained after evaporation of the pentane solution, is now sublimed at 140°–150° C./0.03 mm Hg.

Yield: 0.51 g of colourless 9 (67.1%).
Melting point: softening at ±80° C., melting at 93°–98° C.
$^1$H NMR in $C_6D_6$: δ($Bu^t$) 1.28 (s); δ(CH) 5.93 (s); δ(Et) 0.64 (t) and 1.83 (q); δ(pyNO) 6.17 and 8.10 (d).
Elemental analysis: found (calculated) (%) C 63.03 (63.08); H 8.80 (8.67); N 1.67 (1.84).

EXAMPLE 10

Y{(CH$_3$)$_3$CC(O)CHC(O)C(CH$_3$)$_3$}$_3$.{(CH$_3$)$_3$NO}. (10)

Prepared as described for 7 (in a CH$_2$Cl$_2$/EtOH 1:1 mixture) from 0.64 g (1.0 mmol) of Y(YMHD)$_3$ and 0.22 g (2.0 mmol) of Me$_3$NO.2H$_2$O. The residue, obtained after evaporation of the pentane solution, is now sublimed at 180°–200° C./0.05 mm Hg.

Yield: 0.41 g of colourless 10 (57.7%).
Melting point: 199°–202° C.
$^1$H NMR in CDCl$_3$: δ($Bu^t$) 1.06 (s); δ(CH) 5.58 (s); δ(MeN) 3.33 (s);
Elemental analysis: found (calculated) (%). C 60.48 (60.60); H 9.31 (9.26); N 2.24 (1.96).
STA: melting peak at 196° C.; evaporation from 114°–316° C.; a residue of 1.05% remains afterwards.

EXAMPLE 11

Y{(CH$_3$)$_3$CC(O)CHC(O)C(CH$_3$)$_3$}$_3$.{(C$_6$H$_5$)$_3$PO}. (11)

Prepared as described for 1 from 0.64 g (1.0 mmol) of Y(TMHD)$_3$ and 0.28 g (1.0 mmol) of Ph$_3$PO. The residue, obtained after evaporation of the solvent, is sublimed at 140°–180° C./0.04 mm Hg.

Yield: 0.84 g of colourless 11 (92.3%).
Melting point: 263°–265° C.
$^1$H NMR in CDCl$_3$: δ($Bu^t$) 0.98 (s); δ(CH) 5.58 (s); δ(Ph) 7.42, 7.52 and 7.70 (m).
Elemental analysis: found (calculated) (%) C 66.39 (66.82); H 7.92 (7.86); P 3.26 (3.39).
STA: phase transition peaks at 110° and 166° C.; melting peak at 278° C.; evaporation from 186°–343° C.; a residue of 1.01% remains afterwards.

EXAMPLE 12

Y{(CH$_3$)$_3$CC(O)CHC(O)C(CH$_3$)$_3$}$_3$.{(C$_2$H$_5$)$_3$PO}. (12)

Prepared as described for 1 from 0.64 g (1.0 mmol) of Y(TMHD)$_3$ and 0.134 g (1.0 mmol) of Et$_3$PO. The residue, obtained after evaporation of the solvent, is now sublimed at 150°–180° C./0.25 mm Hg.

Yield: 0.63 g of colourless 12 (82.1%).
Melting point: 267°–270° C.
$^1$H NMR in CDCl$_3$: δ($Bu^t$) 1.01 (s); δ(CH) 5.57 (s); δ(EtP) 1.0–1.2 and 1.65–1.77 (m).
Elemental analysis: found (calculated) (%) C 60.66 (60.63); H 9.51 (9.33); P 3.88 (4.02).
STA: phase transition peak at 116° C.; melting peak at 273° C.; evaporation from 169°–316° C.; a residue of 0.60% remains afterwards.

EXAMPLE 13

Y{(CH$_3$)$_3$CC(O)CHC(O)C(CH$_3$)$_3$}$_3$.{C$_5$H$_5$N}. (13)

0.64 g (1.0 mmol) of Y(TMHD)$_3$ is crystallised from 3 ml of pyridine. The product is air-dried for 6 h.

Yield: 0.56 g of colourless 13 (78.9%).
Melting point: 129°–131° C.
$^1$H NMR in CDCl$_3$: δ($Bu^t$) 1.07 (s); δ(CH) 5.70 (s); δ(py) 7.64, 7.75 and 8.78 (m).
Elemental analysis: found (calculated) (%) C 63.55 (63.61); H 8.69 (8.65); N 2.02 (1.95).
Sublimation: the complex does not sublime as such; at 130°–150° C./0.01 mm Hg dissociation occurs with evaporation of the pyridine; the sublimate consists of Y(YMHD)$_3$ only ($^1$H NMR).

EXAMPLE 14

Y{(CH$_3$)$_3$CC(O)CHC(O)C(CH$_3$)$_3$}$_3$. {(CH$_3$)$_2$NC(O)H}. (14)

0.5 g (0.78 mmol) of Y(TMHD)$_3$ is crystallised from 3 ml of DMF. The product is air-dried for 4 h.

Yield: 0.45 g of colourless 14 (80.8%).
Melting point: 151°–153° C.
$^1$H NMR in CDCl$_3$: δ($Bu^t$) 1.05 (s); δ(CH) 5.66(s); δ(MeN) 2.88 and 2.95 (s); δ(CHO) 8.73 (s).
Elemental analysis: found (calculated) (%) C 60.51 (60.77); H 9.03 (9.00); N 2.11 (1.97).
Sublimation: the complex does not sublime as such; at 130°–160° C./0.02 mm Hg dissociation occurs with evaporation of the DMF; the sublimate consists of Y(TMHD)$_3$ and 0.2 eq of DMF ($^1$H NMR).

EXAMPLE 15

Y{(CF$_3$CF$_2$CF$_2$C(O)CHC(O)C(CH$_3$)$_3$}$_3$.{(CH$_3$)$_2$NCH$_2$CH$_2$N(CH$_3$)CH$_2$CH$_2$N(CH$_3$)$_2$}. (15)

Prepared as described from 1 from 1.22 g (1.25 mmol) of Y(FOD)$_3$ and 0.22 g (1.25 nmol) of the triamine. The residue, obtained after evaporation of the solvent, is now sublimed at 120°–150° C./0.05 mm Hg.

Yield: 1.42 g of beige 15 (99.3%).
Meltng point: 85°–88° C.
$^1$H NMR in CDCl$_3$: δ($Bu^t$) 1.07 (s); δ(CH) 5.95 (s); δ(NMe$_2$) 2.29 (s,br); δ(NMe) 2.23 (s,br); δ(CH$_2$N) 2.54 and 2.72 (m,br).

Elemental analysis: found (calculated) (%) C 40.37 (40.81); H 4.42 (4.62); N 3.60 (3.66).

STA: melting peak at 90° C.; evaporation from 102°–273° C.; a residue of 0.22% remains afterwards.

EXAMPLE 16

Simultaneous Thermal Analysis (STA) of Y(β-diketonate)$_3$-ligand complexes.

Simultaneous Thermal Analysis (STA) of various Y(β-diketonate)$_3$-ligand adducts is carried out at atmospheric pressure in a nitrogen flow of 40 sccm; the heating rate was 20° C./min from room temperature to 600° C. Results are presented in Table 1.

TABLE 1

| Compound | Melting °C. | Start Evaporation °C. | End Evaporation °C. | Residue % |
|---|---|---|---|---|
| Y(TMHD)$_3$ | 177 | 129 | 267 | 4.40 |
| 1 | 188 | 155 | 293 | 0.55 |
| 2 | 269 | 166 | 353 | 1.22 |
| 7 | 179 | 146 | 288 | 0.71 |
| 8 | 104 | 146 | 306 | 1.63 |
| 9 | 106 | 149 | 297 | 2.06 |
| 10 | 196 | 114 | 316 | 1.05 |
| 11 | 278 | 186 | 343 | 1.01 |
| 12 | 277 | 169 | 316 | 0.60 |
| 15 | 90 | 102 | 273 | 0.22 |

Table 1 shows selected results of Simultaneous Thermal Analyses of some compounds according to the invention and of Y(TMHD)$_3$. The numbers refer to the numbers of the structural formulae in the detailed description.

EXAMPLE 17

Sublimation of Y(β-diketonate)$_3$-ligand adducts.

Sublimation of various Y(β-diketonate)$_3$-ligand adducts is performed at reduced pressure (0.01–0.05 mm Hg) and at temperatures of 90°–200° C. Results are presented in Table 2.

TABLE 2

| Compound (100 mg) | Melting point °C. | Sublimation point at 0.01–0.05 mm Hg °C. | Ligand in sublimate eq |
|---|---|---|---|
| Y(TMHD)$_3$ | 169–172.5 | 130–160 | — |
| Y(FOD)$_3$ · H$_2$O | 108–112 | 130–160 | — |
| 1 | 185–188 | 160–170 | 1.0 |
| 2 | 260–262 | 180–200 | 1.0 |
| 3 | 145–150 | 150 | trace |
| 4 | 60–63 | 90–160 | 0.4 |
| 5 | 55–60 | 90–130 | 2.4 |
| 6 | 156–158 | 135–160 | 0.3 |
| 7 | 175–177 | 150–160 | 1.0 |
| 8 | 97–100 | 140 | 1.0 |
| 9 | 93–98 | 140–150 | 1.0 |
| 10 | 199–202 | 180–200 | 1.0 |
| 11 | 263–265 | 140–180 | 1.0 |
| 12 | 267–270 | 150–180 | 1.0 |
| 13 | 129–131 | 130–150 | 0.0 |
| 14 | 151–153 | 130–160 | 0.2 |
| 15 | 85–88 | 120–150 | 1.0 |

Table 2 shows volatilities and melting points of some adducts according to the invention, as well as those of commercial Y(TMHD)$_3$ and of Y(FOD)$_3$.H$_2$O. The numbers refer to the numbers of the structural formulae in the detailed description.

EXAMPLE 18

Vapour pressure measurements on Y(β-diketonate)$_3$-ligand adducts.

Vapour pressure measurements on various Y(β-diketonate)$_3$-ligand adducts are carried out at temperatures of 90°–180° C. and at a nitrogen background pressure of less than 0.01 torr. Volatile impurities, which may be present, are removed by pumping several times for 30 seconds at lowered pressure (<0.01 torr), previous to the measurement. Results are presented in FIG. 1 and Table 3.

TABLE 3

| Compound | Temperature range °C. | A | B | ΔH$_s$ kg/mol |
|---|---|---|---|---|
| Y(TMHD)$_3$ | 140–170 | 13.919 | 6.269 | 120 |
|  | 180–200 | 8.30 | 3.71 | 71 |
| 1 | 140–180 | 15.396 | 6.929 | 133 |
| 7 | 140–170 | 13.695 | 6.172 | 118 |
| 8 | 120–180 | 11.687 | 5.259 | 101 |
| 9 | 120–180 | 14.607 | 6.487 | 124 |
| 15 | 90–170 | 5.865 | 2.466 | 47 |

Table 3 shows temperature dependencies of the vapour pressures of some compounds according to the invention, as well as those of commercial Y(TMHD)$_3$. The numbers refer to the numbers of the structure formulae in the detailed description. The vapour pressure data are tabled according to the following equation: $\text{Log}_{10}[P(T)/P_0]=A-1000\,B/T$, with P is the pressure in Torr and T is the temperature in degrees Kelvin, $P_0=1$. From B the evaporation enthalpy $\Delta H_s$(KJ/mol) is calculated.

EXAMPLE 19

MOCVD deposition of Y$_2$O$_3$ from

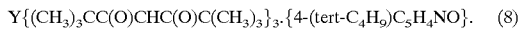

$$Y\{(CH_3)_3CC(O)CHC(O)C(CH_3)_3\}_3 \cdot \{4\text{-(tert-}C_4H_9)C_5H_4NO\}. \quad (8)$$

In a hot-wall MOCVD apparatus, a dry N$_2$ flow (83 sccm) was led over Y{(CH$_3$)$_3$CC(O)CHC(O)C(CH$_3$)$_3$}$_3$.{4-(tert-C$_4$H$_9$)C$_5$H$_4$NO} at 160° C., and mixed with N$_2$ (83 sccm) and O$_2$ (100 sccm) before entering the reactor chamber. The deposition was performed on a MgO substrate, which is attached to a mass balance by a quartz wire. This balance was protected by a flow of N$_2$ (17 sccm). The deposition was performed at a substrate temperature of 850° C. and at a reactor pressure of 2 torr. The growth rate was 3.3 mg/cm$^2$/hr.

EXAMPLE 20

Dy(TMHD)$_3$.4-tBuPyNO

A dry Schlenk tube was charged under inert atmosphere with Dy(TMHD)$_3$ (2.50 g, 3.51 mmol) and 4-tert-butyl-pyridine-N-oxide (0.53 g, 3.51 mmol). Dry toluene (40 cm$^3$) was added to the tube against a strong nitrogen flush. A clear, slightly green solution with faint metallic lustre rapidly formed on stirring. The solution was stirred at ambient temperature overnight before removing the stirrer bar. Solvent was then removed under vacuum until at a minimal level of remaining solvent, crystals formed on the sides of the tube. The solvent was warmed to dissolve the solids then gradually cooled to −20° C. to crystallise. The solution set as a near-solid mass of crystals (2.678 g) from which only a small amount of toluene could be removed.

Melting point 109° C. (by STA) C/H/N found versus (calculated) C 59.71 (59.42) wt %, H 8.28 (8.12) wt %, and N 1.61 (1.62) wt % STA indicated the material to be solvent wet as indicated by a slight weight loss at below 100° C. associated with a small exothermic feature. Further weight loss onsets at 187° C. and proceeds in a single, smooth, endothermic step to a residue of 3 wt % complete by 310° C. This indicates the material to sublime intact with accompanying minor amounts of decomposition. The material should thus be suitable for use in the MOCVD rig where the volatilisation occurs at lower temperature under reduced pressure. Material was left in the open laboratory overnight and the STA trace obtained. There was less evidence for the presence of volatile solvent. The melting point and evaporation range were unchanged, showing the material to have good stability towards hydrolysis in ambient air. The residue was at 2.8 wt % slightly smaller.

A small sample (0.509 g) of the material was charged to a Schlenk tube fitted with a cold finger and subjected to vacuum sublimation at 0.4 mBar, 120° C. rising to 150° C. once the sample had melted. Sublimation rapidly yielded a fine white powder and left a minimal residue. The powder (0.39 g recovered, problems with static) was submitted for STA. The trace obtained was identical to those described above, save that a low wet residue, 1.8 wt % remained. This shows the material to sublime intact at temperatures consistent with use in an LP-MOCVD rig.

A sample of $Dy(TMHD)_3$ obtained commercially (Lancaster Synthesis) was subjected to STA under the same conditions as used above. The sample showed melting point 180° C. and evaporated to 1 wt % residue over the range 165°–282° C. This shows the adduct complex to be lower melting and only slightly less volatile.

EXAMPLE 21

$Er(TMHD)_3.4$-tBuPyNO

A sample of $Er(TMHD)_3$ (2.53 g, 3.53 mmol) was charged under inert atmosphere to a Schlenk tube-along with 4-tert-butyl-pyridine-N-oxide (0.53 g, 3.53 mmol). Toluene (20 cm$^3$) was, added against rapid nitrogen flush. An orange-pink solution formed after brief stirring. The stirrer bar was removed after about one hour and the solvent removed under vacuum to leave a thick orange oil. The oil was taken up in minimum hexane (10 cm$^3$) and refrigerated. Overnight refrigeration to −20° C. produced a small batch of crystals and some white powder. Further solvent was removed under vacuum and the solution once more refrigerated. A large mass of pink crystals was recovered (1.751 g).

C/H/N analysis, found versus (calculated) for $Er(TMHD)_3$. 4-tBuPyNo, C 57.79 (58.11), H 8.32 (8.06) and N 1.61 (1.61) wt %.

STA showed this material to melt at 105° C. before evaporating over the range 172°–300° C. to a low residue (1.8 wt %). Material exposed to ambient air overnight gave, within experimental error an identical result, demonstrating the good stability towards hydrolysis by ambient air.

The material (0.541 g) was loaded into a Schlenk tube fitted with a cold finger and subjected to vacuum sublimation at 0.4 mBar, 120°–150° C. About 0.47 g of a glassy pink material was recovered.

The sublimate was subjected to STA under identical conditions to those described above. There was evidence for some dissociation on sublimation, but the melting point increased only slightly (to 109° C.) and the sublimation range remained the same, with a lower ultimate residue (1.1%). There is thus good evidence to suggest that this material sublimes intact or near intact.

EXAMPLE 22

$Y(HFA)_3.4$-tBuPyNO

HFA is 1,1,1,5,5,5-hexafluoroacetylacetonate (or 1,1,1,5, 5,5-pentane-2,4-dionate).

A dry Schlenk tube was charged under inert atmosphere with $Y(HFA)_3$ (5.165 g, 7.28 mmol) and 4-tert-butyl-pyridine-N-oxide (1.098 g, 7.27 mmol). $CH_2Cl_2$ (120 cm$^3$) was added against nitrogen flush. The resulting cloudy solution was stirred overnight at ambient temperature under a low flow of nitrogen. The solvent was removed under vacuum and the resulting white powder extracted with refluxing hexane (40 cm$^3$) and separately with a similar volume of refluxing toluene. The material was of low solubility in both solvents, but white, cubic crystals were obtained on cooling in each case.

The recrystallised samples and the white powder were all subjected to STA. This showed the materials to be essentially identical, with that recrystallised from hexane the purest. The material recrystallised from hexane had a broad melt at 102° C. An endothermic event associated with a weight loss, corresponding to intact evaporation began at about 200° C. At about 265° C. an exothermic event was observed, completed by 280° C. The weight loss continued smoothly through this event, finishing at 300° C., leaving a low 2.7% residue). This shows the material to be a good MOCVD precursor, if not ideal. It is low melting, and stable to well about 200° C. and can be successfully evaporated under typical MOCVD conditions.

Other modifications of the present invention will be apparent to those skilled in the art.

We claim:

1. In an yttrium-containing material deposition process, wherein the deposition process is a vapour deposition process, the improvement comprising the use of an yttrium β-diketonate/donor ligand adduct to deposit the material on a substrate and wherein the donor ligand is an N-oxide.

2. The process according to claim 1 wherein the vapour deposition process is a metal-organic chemical vapour deposition (MOCVD) process.

3. The process according to claim 1 wherein the yttrium β-diketonate/donor ligand adduct has a melting point of less than about 150° C.

4. The process according to claim 3 wherein the yttrium β-diketonate/donor ligand adduct has a melting point of less than about 125° C.

5. The process according to claim 4 wherein the yttrium β-diketonate/donor ligand adduct has a melting point of less than about 100° C.

6. The process according to claim 1 where in the N-oxide is a pyridine N-oxide.

7. In a method of using an yttrium β-diketonate/donor ligand adduct in an yttrium containing material deposition process, wherein the deposition process is a vapour deposition process, the improvement comprising the steps of providing a vapor of said adduct and depositing the material on a substrate, wherein the donor ligand is an N-oxide.

8. The method according to claim 7 wherein the yttrium β-diketonate/donor ligand adduct has a melting point of less than about 150° C.

9. The method according to claim 8 wherein the yttrium β-diketonate/donor ligand adduct has a melting point of less than about 125° C.

10. The method according to claim 9 wherein the yttrium β-diketonate/donor ligand adduct has a melting point of less than about 100° C.

11. The method according to claim 7 wherein the N-oxide is a pyridine N-oxide.

* * * * *

UNITED STATES PATENT AND TRADEMARK OFFICE
CERTIFICATE OF CORRECTION

PATENT NO. : 5,837,321
DATED : November 17, 1998
INVENTOR(S) : Klaas Timmer et al.

It is certified that error appears in the above-identified patent and that said Letters Patent is hereby corrected as shown below:

On the title page, item [54] and col. 1 line 5, delete "FORM" and insert therefor: ---FROM---.

Signed and Sealed this

Twentieth Day of April, 1999

Attest:

Q. TODD DICKINSON

*Attesting Officer*  *Acting Commissioner of Patents and Trademarks*